US006206825B1

(12) United States Patent
Tsuyuki

(10) Patent No.: US 6,206,825 B1
(45) Date of Patent: Mar. 27, 2001

(54) ILLUMINATION SYSTEM FOR ENDOSCOPES AND AN ENDOSCOPE HAVING THE ILLUMINATION SYSTEM

(75) Inventor: Hiroshi Tsuyuki, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/231,787

(22) Filed: Jan. 15, 1999

Related U.S. Application Data

(62) Division of application No. 08/671,537, filed on Jun. 27, 1996, now Pat. No. 5,882,296.

(30) Foreign Application Priority Data

Jun. 29, 1995 (JP) .................................................. 7-184981

(51) Int. Cl.[7] ...................................................... A61B 1/07
(52) U.S. Cl. ........................ 600/182; 600/129; 600/130; 385/117
(58) Field of Search ..................................... 600/182, 177, 600/178, 128, 129, 130; 385/115–117; 362/554, 556, 574

(56) References Cited

U.S. PATENT DOCUMENTS

| | | | |
|---|---|---|---|
| 3,556,085 | * | 1/1971 | Takahashi ............................ 600/129 |
| 3,941,121 | * | 3/1976 | Olinger et al. ....................... 600/167 |
| 4,558,691 | | 12/1985 | Okada . |
| 4,706,653 | | 11/1987 | Yamamoto . |
| 4,747,681 | | 5/1988 | Ohkuwa . |
| 4,765,313 | | 8/1988 | Kamakura . |
| 4,787,370 | | 11/1988 | Kanamori . |
| 4,790,295 | * | 12/1988 | Tashiro ................................. 600/176 |
| 4,802,460 | | 2/1989 | Ohkuwa et al. . |
| 4,807,597 | * | 2/1989 | Tsuno et al. ......................... 600/177 |
| 4,856,495 | | 8/1989 | Tohjoh et al. . |
| 4,860,732 | | 8/1989 | Hasegawa et al. . |
| 4,918,521 | * | 4/1990 | Yabe et al. ........................... 600/130 |
| 4,958,932 | * | 9/1990 | Kegelman et al. .................. 600/182 |
| 4,986,642 | | 1/1991 | Yokota et al. . |
| 5,050,974 | | 9/1991 | Takasugi et al. . |
| 5,208,702 | | 5/1993 | Shiraiwa . |
| 5,305,736 | * | 4/1994 | Ito ........................................ 600/176 |
| 5,423,312 | * | 6/1995 | Siegmund et al. .................. 600/178 |
| 5,547,457 | | 8/1996 | Tsuyuki et al. . |
| 5,730,702 | * | 3/1998 | Tanaka et al. ....................... 600/180 |

FOREIGN PATENT DOCUMENTS 2-74912   3/1990   (JP) .

* cited by examiner

Primary Examiner—John P. Leubecker
(74) Attorney, Agent, or Firm—Pillsbury Madison & Sutro LLP

(57) ABSTRACT

An illumination system for endoscopes has a light guide bundle constructed and arranged to illuminate an object to be observed. The light guide bundle is extended in an axial direction of the endoscope and branched into a plurality of branch portions in a frame which is adapted to be disposed inside of the endoscope. Each of the branch portions have a crescent-shaped cross-section at a mid-portion along the axial direction of the endoscope and each of the branch portions have at least one bent portion in which a protective glass plate is disposed on each exit surface of the branch portions. An endoscope system includes the above illumination system.

10 Claims, 12 Drawing Sheets

ILLUMINATION SYSTEM FOR ENDOSCOPES AND AN ENDOSCOPE HAVING THE ILLUMINATION SYSTEM

This is a division of Application Ser. No. 08/671,537, filed Jun. 27, 1996, now U.S. Pat. No. 5,882,296.

BACKGROUND OF THE INVENTION a) Field of the Invention

The present invention relates to an objective optical system for endoscopes, and more specifically to an objective optical system for endoscopes which is configured to allow a plurality of adapter optical systems to be attached and detached thereto and therefrom for changing a direction toward a visual field, a field angle and an observation distance.

b) Description of the Prior Art

Conventionally, medical endoscopes which permit inserting elongated insert sections into living bodies for observing organs in the living bodies and passing forceps through forceps channels for sampling tissues of living bodies for detailedly diagnosing diseased parts in detail are widely used. Industrial endoscopes which permit observation and inspections of interiors of boilers, turbines, chemical plants and so on are widely known in industrial fields.

Attached to an industrial endoscope, in particular, is a direct view type adapter for observing a diseased part which is located in the longitudinal direction before the insert section or a side-view type adapter for observing an inside wall which is located sideways in a direction perpendicular to the inserting direction. In practice, one simultaneously selects an adapter which has a field angle that is optimum for a location to be observed and another adapter which has an optimum observation distance (or a depth of field) and so on.

It is effective from an economical viewpoint to configure such an expensive endoscope as a tip adapter type endoscope which can be equipped with adapters having a direction of a visual field, a field angle and an observation distance matched with a location to be observed.

Also widely used in the industrial fields are electronic endoscopes which provide images of qualities remarkably improved owing to progress made in solid-state image pickup devices (CCD's).

A conventionally known example of such electronic endoscopes is an electronic endoscope disclosed by Japanese Patent Kokai Publication No. Hei 2-74,912 which has a composition shown in FIG. 1. This conventional electronic endoscope has no mechanism of the tip adapter type described above and is not versatile in the industrial fields. When an attempt is made to configure this electronic endoscope as the tip adapter type by dividing a lens system thereof into a subsystem which is located before an aperture'stop S and replaceable with an adapter, and another subsystem located after the aperture stop S, for example, it is necessary to dispose a light guide to be used in an illumination system at a location of a lens unit L. A reason to select this disposition is that it is optimum to dispose a light guide G so that it turns below a side-viewing prism P as shown in FIG. 2 for attaching a side-viewing adapter.

When the light guide is disposed at the location of the lens unit L in the electronic endoscope disclosed by Japanese Patent Kokai Publication No. Hei 2-74,912, an objective optical system of this electronic endoscope has a large outside diameter at its tip. For disposing the light guide without enlarging its outside diameter, it is necessary to reduce an outside diameter of the lens unit L or a number of optical fibers which are to be used for composing a light guide. As a result, rays are eclipsed by the lens unit L or illuminating rays are reduced, thereby making brightness insufficient.

On the other hand, there is known an objective optical system for tip adapter type electronic endoscopes which has a composition shown in FIG. 3. This objective optical system for tip adapter type endoscopes is configured to concentrate all light guides at the location of the lens unit L for correcting the defect of the electronic endoscope disclosed by Japanese Patent Kokai publication No. Hei 2-74, 912.

In the recent years where images of having higher qualities and full-screen sizes are strongly demanded, it is expected that electronic endoscopes which can provide images suited for display on high definition televisions (HDTV's) will be adopted in the near future.

For obtaining images of such high qualities, however, it is necessary to configure picture elements so as to have a smaller size, or lower illuminance per picture element on an image surface, thereby making it difficult to maintain the conventional image brightness. Further, it is known that depths of field are reduced by reducing sizes of picture elements.

For correcting the defects described above, it is necessary to reserve a required depth of field by enlarging an F number of an objective lens system and compensate for brightness by increasing the number of optical fibers that are used for making the light guide.

In the field of the endoscopes which should desirably have smaller diameters, however, it is undesirable to increase the number of optical fibers that are used for making the light guide since such increase results in enlarging the outside diameters of the endoscopes. In the case of the objective optical system for the tip adapter type of electronic endoscopes illustrated in FIG. 3, the objective optical system has an outside diameter which is enlarged by increasing the number of optical fibers. When the objective optical system for tip adapter type endoscopes is configured to provide a full-size screen, it may not accept an increase the heights of rays caused by enlarging an image side and allow a visual field to be eclipsed. In FIG. 3, the reference symbol AD represents an adapter lens system and the reference symbol M designates a master lens system.

SUMMARY OF THE INVENTION

A primary object of the present invention is to provide an objective optical system for endoscopes which permits using lens elements having relatively small outside diameters and reducing outside diameters of tips of endoscopes without reducing numbers of optical fibers to be used for composing light guides, and more specifically an objective optical system for tip adapter type endoscopes.

The objective optical system according to the present invention is characterized in that it is disposed, in an object side tip of an endoscope, in parallel with an illumination optical system which is inserted in a longitudinal direction and tied up in a bundle, and that it comprises lens elements which are disposed in the object side tip of the endoscope and have an outside diameter smaller than that of lens elements located in the vicinity of an image pickup device disposed on the object side in the endoscope.

The objective optical system for endoscopes according to the present invention which has the object side tip having a small outside diameter permits reducing outside diameters of tips of endoscopes without reducing numbers of optical fibers which are to be used for composing light guides.

Further, the objective optical system for endoscopes according to the present invention is characterized in that it is configured as an adapter type objective optical system for endoscopes having a tip to and from which an adaptor comprising an aperture stop for the objective optical system can freely be attached and detached.

The objective optical system for endoscopes according to the present invention consists, as exemplified in FIG. 4, of a lens unit A which is disposed as a tip on the object side and a lens unit B which is disposed on a side of an image pickup device; the lens unit A having an outside diameter smaller than that of the lens unit B.

A tip adapter lens system AD having a small outside diameter is freely attachable and detachable, as shown in FIG. 5, to and from the object side of an objective optical system (master lens system) M which is composed of the lens unit A and the lens unit B shown in FIG. 4.

An image of an object to be observed is allowed by the adapter lens system AD to pass through an aperture stop S1 and fall nearly perpendicularly onto an image receiving surface of an image pickup device disposed in the objective optical system (master lens system) M. In other words, a nearly telecentric optical system is composed of the adapter lens system AD and the master lens system M.

Furthermore, the optical objective system for endoscopes according to the present invention is characterized in that it is configured so as to satisfy the following conditions (1) and (2):

$$1.4 \leq f_A/f_B \leq 7.2 \quad (1)$$

$$2.3 \leq f_A/f_M \leq 10 \quad (2)$$

wherein the reference symbol $f_A$ represents a focal length of the lens unit A, the reference symbol $f_B$ designates a focal length of the lens unit B and the reference symbol $f_M$ denotes a focal length of the objective optical system (master lens system) M.

Moreover, the objective optical system for endoscopes according to the present invention is characterized in that the lens unit A having a small diameter comprises a cemented lens component which consists of a negative lens element and a positive lens element, and is configured so as to satisfy the following conditions (3) and (4):

$$n_1 > n_2 \quad (3)$$

$$v_{d1} < v_{d2} \quad (4)$$

wherein the reference symbols $n_1$ and $n_2$ represent refractive indices of the negative lens element and the positive lens element respectively of the cemented lens component, and the reference symbols $v_{d1}$ and $v_{d2}$ designate Abbe's numbers of the negative lens element and the positive lens element respectively of the cemented lens component.

DETAILED DESCRIPTION OF THE PREFERRED EMBODIMENTS

Figure 4:
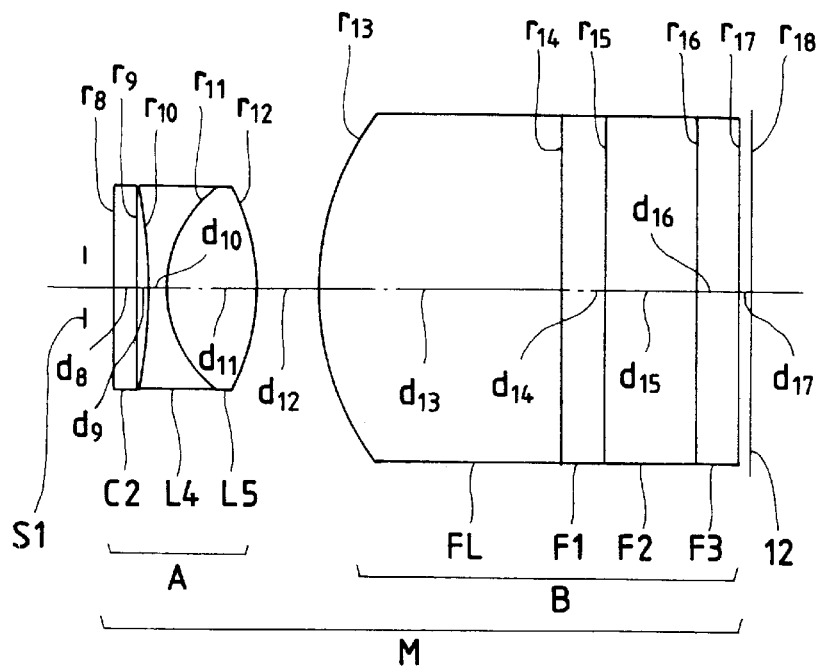
FIG. 4 shows a sectional view illustrating a composition of a first embodiment of the objective optical system for endoscopes according to the present invention.

The objective optical system for endoscopes according to the present invention consists, as exemplified in FIG. 4, of a lens unit A which is disposed as an object side tip and a lens unit B which is disposed on a side of an image pickup device; the lens unit A having an outside diameter smaller than that of the lens unit B.

Figure 5:
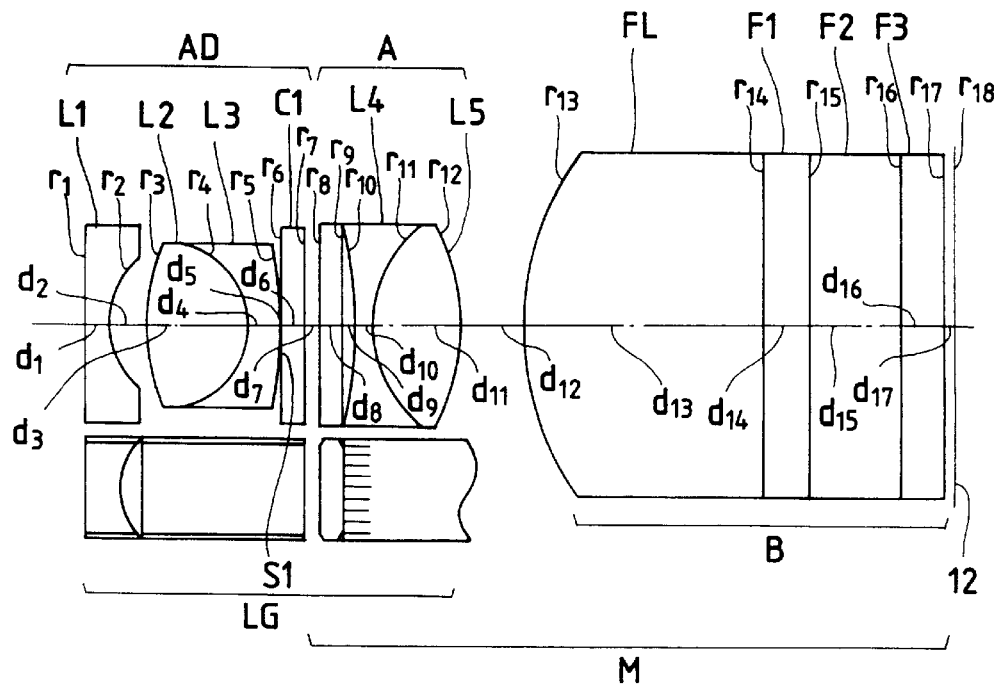
FIG. 5 shows a sectional view illustrating the first embodiment of the objective optical system according to the present invention in a condition where an adapter lens system is attached to the objective optical system.

A tip adapter lens system AD is freely attachable and detachable, as shown in FIG. 5, to and from the object side of an objective optical system (master lens system) M which is composed of the lens unit A and the lens unit B shown in FIG. 4. Such a lens system is also referred to as an adapter type objective system.

The objective optical system (master lens system) M and the adapter lens system compose a nearly telecentric system wherein an image of an object to be observed is allowed by the adapter lens system AD to pass through an aperture stop S1 and fall nearly perpendicularly onto an image receiving surface 12 of an image pickup device 13.

Further, the optical system according to the present invention is characterized in that it is configured so as to satisfy the following conditions (1) and (2):

$$1.4 \leq f_A/f_B \leq 7.2 \quad (1)$$

$$2.3 \leq f_A/f_M \leq 10 \quad (2)$$

wherein the reference symbol $f_A$ represents a focal length of the lens unit A, the reference symbol $f_B$ designates a focal length of the lens unit B and the reference symbol $f_M$ donotes a focal length of the objective optical system (master lens system) M.

The condition (1) defines a ratio between the focal length of the lens unit A and that of the lens unit B. Images formed by a simultaneous type electronic endoscope which uses a color mosaic filter may be affected by color shading or luminance shading. Since such a defect is dependent on angles of incidence of rays on image pickup surfaces, it is desirable that an objective optical system for electronic endoscopes is a telecentric system.

If the upper limit of 7.2 of the condition (1) is exceeded, the lens unit B must have a short focal length for configuring the objective optical system so as to satisfy the telecentric condition and an off axial principal ray will have a large inclination angle. Accordingly, the lens unit A will have a function of a lens which refracts rays having very low heights and must use a lens element having a very short radius of curvature or a high refractive power. As a result, the lens unit A will have a small outside diameter and can hardly be manufactured in practice. Further, a strong refractive power of the lens unit A is undesirable for correction of aberrations since such a strong power degrades balance of coma. For correcting coma, it is necessary to weaken the refractive power of the lens unit A by reserving a wide airspace therein. However, such an airspace is undesirable since the airspace makes it difficult to configure the objective optical system so as to satisfy the telecentric condition and prolongs a total length thereof.

If the lower limit of 1.4 of the condition (1) is exceeded, the lens unit B will have a long focal length and the offaxial principal ray will be high on the lens unit A, whereby it must have a large outside diameter contrary to the object of the present invention. Further, when an adapter lens system is to be attached to the tip of the objective optical system for composing an adapter type electronic endoscope as described above, a sectional area of a light guide LG which is to be disposed in an objective optical system frame of the endoscope is inevitably restricted by the lens unit since it is desirable to dispose the light guide in the vicinity of the lens unit A. Accordingly, a large outside diameter of the lens unit A is undesirable since it results in insufficiency of brightness by narrowing an area allowed for a light guide or enlarges an outside diameter of the tip of the endoscope.

The condition (2) defines a ratio between the focal length of the lens unit A and that of the objective optical system (master lens system). If the upper limit of 10 of the condition (2) is exceeded, the master lens system M will have a focal length too short for obtaining the objective optical system according to the present invention. In case of a telecentric optical system, an aperture stop is disposed at a location of a front focal point of a lens unit disposed after the aperture stop, or the master lens system M. Accordingly, the master lens system has a short total length but the adapter lens system undesirably has a large outside diameter when the upper limit of the condition (2) is exceeded. When an attempt is made to lower rays by strengthening a refractive power, for example, of a cemented lens component consisting of lens elements L2 and L3 disposed in the adapter lens system shown in FIG. 5, it is necessary to impart a very strong refractive power to this cemented lens component since rays are high on this lens component which is disposed close to the aperture stop. As a result, it will be difficult to manufacture this cemented lens component in practice and spherical aberration will undesirably be aggravated. When the cemented lens component is disposed apart from the aperture stop and has a weakened refractive power, in contrast, the adapter lens system will undesirably have a large outside diameter and a long total length.

If the lower limit of 2.3 of the condition (2) is exceeded, the master lens system M will have a long focal length for configuring the objective optical system so as to satisfy the telecentric condition. As a result, the master lens system will have a large total length. Accordingly, an endoscope which has a tip bending mechanism will have a remarkably prolonged non-flexible distal end which is a fatal defect for an endoscope. Further, the offaxial principal ray will have too small an inclination angle and the lens unit A will undesirably tend to have a large outside diameter.

It is desirable that the lens unit A which comprises at least one cemented lens component and has a positive refractive power as described above is configured so as to have a composition described below. Speaking concretely, it is desirable to compose the lens unit A, in order from a side of the aperture stop, of a negative lens element L4 and a positive lens element L5 which has at least one surface convex toward an image surface.

In FIG. 5, asymmetry of strong coma produced by the negative lens element L1 disposed in the adapter lens system is corrected favorably by the surface of the lens element which is convex toward the image surface ($r_{12}$ in FIG. 5). Further, spherical aberration and curvature of field which are produced by the positive lens element disposed in the adapter lens system AD and the master lens system M are corrected to practically allowable levels by a negative function of the cemented surface ($r_{11}$ in FIG. 5) formed between the lens elements L4 and L5 of the cemented lens component disposed in the lens unit A.

Further, it is desirable, for the cemented lens component L4, L5 or the lens unit A comprising at least one cemented lens component and having a positive refractive power, to compose the cemented lens component, in order from the side of the aperture stop S1, of the negative lens element L4 and the positive lens element L5 having at least one surface convex toward the image surface so as to satisfy the following conditions (3) and (4):

$$n_1 > n_2 \quad (3)$$

$$v_{d1} > v_{d2} \quad (4)$$

wherein the reference symbols $n_1$ and $n_2$ represent refractive indices of the negative lens element and the positive lens element respectively of the cemented lens component, and the reference symbols $v_{d1}$ and $v_{d2}$ designate Abbe's numbers of the negative lens element and the positive lens element respectively of the cemented lens component.

The conditions (3) and (4) are required for correcting chromatic aberration produced by a front lens unit disposed before the aperture stop, longitudinal chromatic aberration in particular practically favorably, with the cemented lens component described above. Though this chromatic aberration can be corrected to a certain degree with the cemented lens component disposed in the front lens unit, it is difficult to correct the chromatic aberration sufficiently favorably since the cemented lens component is disposed in the vicinity of the aperture stop. For this reason, correction of the chromatic aberration is aided by the cemented lens component used in a rear leas unit disposed in the image side of the aperture stop.

When the conditions (3) and (4) are satisfied by the cemented lens component, it is possible to Configure the master lens system M so as to have a small outside diameter, and correct practically favorably aberrations which are produced by the objective optical system as a whole consisting of the adapter lens system AD and the master lens system M.

Figure 1:
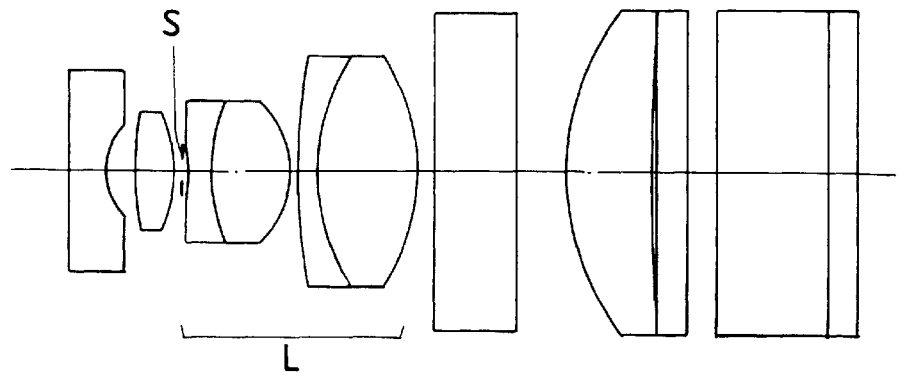
FIG. 1 shows a sectional view illustrating a composition of a conventional objective optical system for endoscopes.
Figure 2:
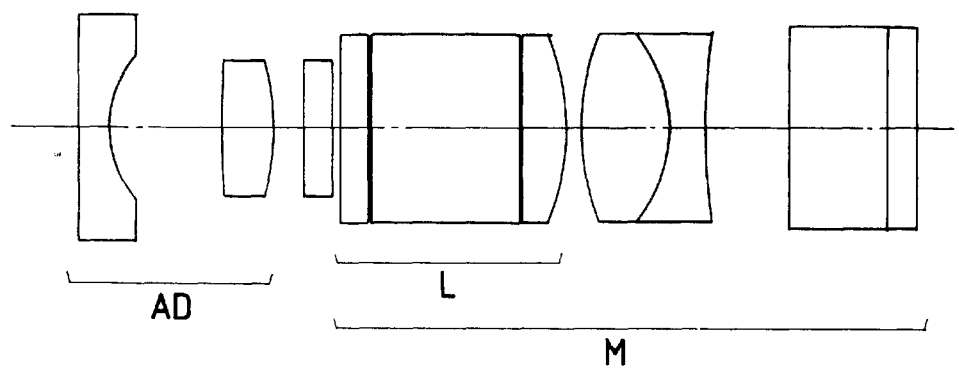
FIG. 2 shows a sectional view illustrating a composition of another conventional objective optical system for endoscopes.
Figure 3:
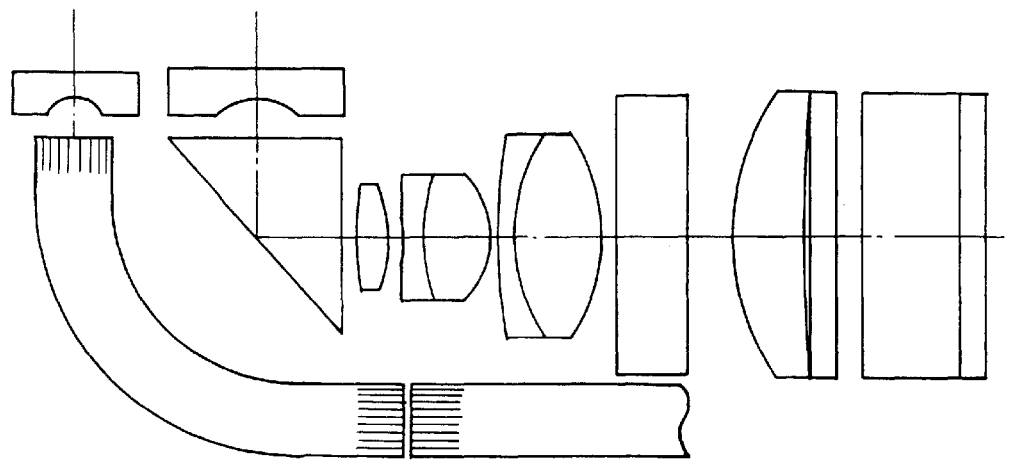
FIG. 3 shows a sectional view illustrating a composition of still another objective optical system for endoscopes.
Figure 6:
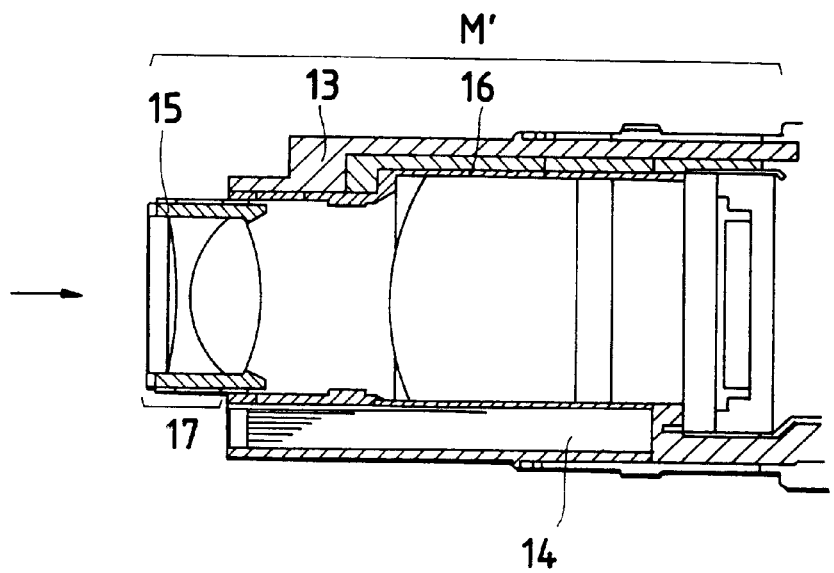
FIG. 6 shows a sectional view illustrating a composition of a master unit which comprises the objective optical system for endoscopes according to the present invention.
Figure 7:
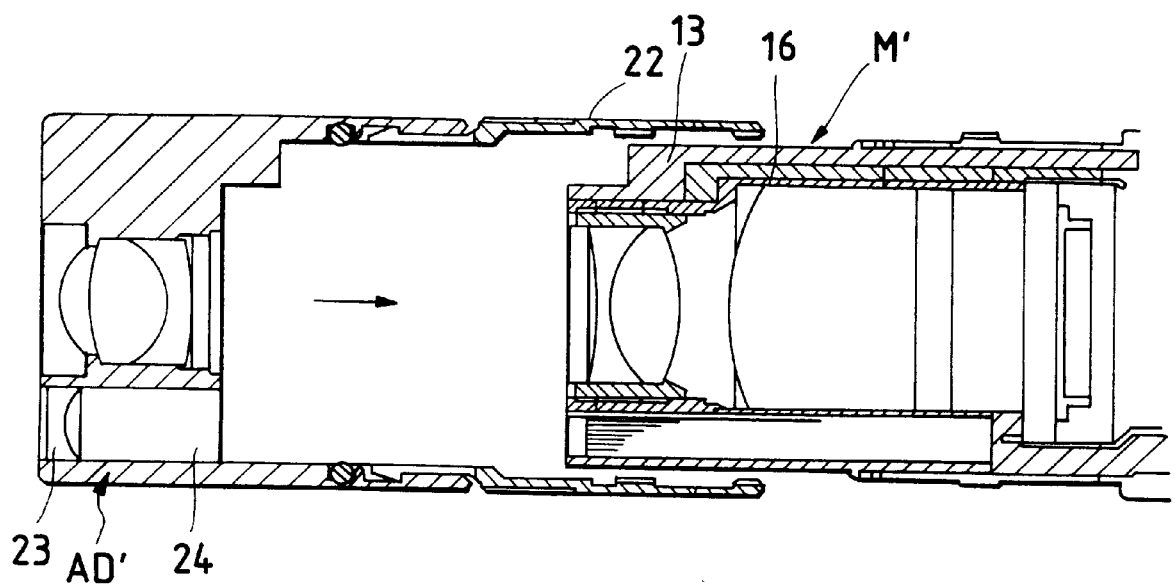
FIG. 7 shows a sectional view illustrating a condition where an adapter unit which comprises the adapter lens system according to the present invention is attached to the master lens unit shown in FIG. 6.

Now, description will be made of the tip adapter type endoscope according to the present invention. Shown in FIGS. 6 and 7 are sectional views illustrating a composition of the tip adapter type endoscope according to the present invention: FIG. 6 showing only the master unit M, whereas FIG. 7 showing a combination of the master unit M' and a tip adapter unit AD' comprising an adapter lens system AD. The master unit M' shown in FIG. 6 consists of the above-mentioned master lens system M which is disposed in a master unit frame 13 and a light guide 14 which passes therethrough. The master unit M' is further equipped with a focus adjusting frame 15 which is adjustably fitted, for example by screwing, in a master lens system receiving frame 16. Further, integrally fitted in the focus adjusting frame 15 is a focus adjusting lens unit (the lens unit A in FIG. 1) which is movable back and forth in a direction along an optical axis together with the focus adjusting frame 15 which is moved relatively to the master lens receiving frame 16 by a moving means, for example, of a screw type. By this focus adjusting mechanism, the master unit M' is adjusted to optimum focused conditions. For this adjustment, it is generally desirable to focus the master lens system on infinite distance so as to minimize a variation in focused condition between the master lens system M and the adapter lens system AD. For this reason, it is effective to select a finite distance for adjusting a focused condition of the master unit M' by using a jig lens or the like (not shown). When variations of focused conditions are too large among adapter lens systems AD which are to be used in combination with the master lens system M, the focused conditions can be adjusted as described below. A means for moving adapter lens systems in the direction along the optical axis is disposed in an adapter unit AD' and the variations of the focused conditions are adjusted by this moving means. For example, the focused conditions can be adjusted by reserving an adjustable airspace between the negative lens element L1 and the cemented lens component consisting of the lens elements L2 and L3 shown in FIG. 5 and moving the lens elements in the axial direction of the endoscope. Since the airspace reserved between the lens element L1 and the cemented lens component consisting of the lens elements L2 and L3 has a very large correction coefficient for the positions of focus, these positions can be moved by slightly moving this airspace in the axial direction.

An adapter unit for observing an object located at a short distance or a long distance can be prepared by adjusting the airspace for intentional change of a position of focus. A more adequate observation range can be obtained by selecting different apertures of the aperture stop for the short distance and the long distance.

A desired direction toward a visual field, a desired field angle and a desired observation distance can be obtained by integrating the master unit M' having an adjusted position of focus with the adapter unit AD' as shown in FIG. 7. Disposed in the adapter unit AD' are the adapter lens system and an adapter side illumination system 23, 24. The adapter unit AD' having such a composition is freely attachable and detachable to and from the master unit M' with an adapter fitting frame 22 or the like. The adapter fitting frame 22 is attached to the master unit M' by a means such as a knurling tool and the adapter unit AD' is equipped with a means for preventing it from coming off.

Figure 8A:
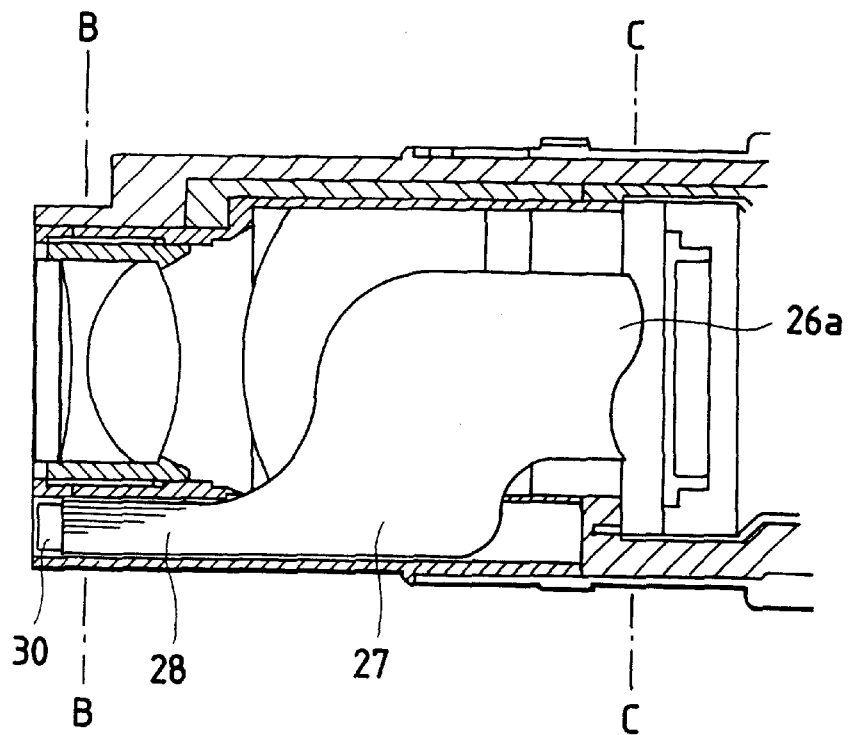
FIGS. 8A, 8B and 8C show views illustrating a condition of a light guide disposed in the master unit shown shown in FIG. 6.
Figure 8B:
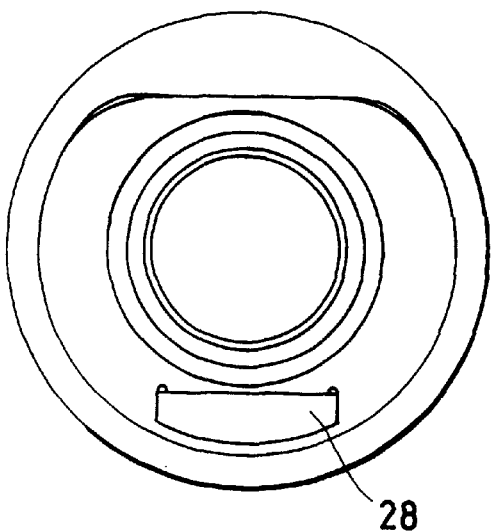
Figure 8C:
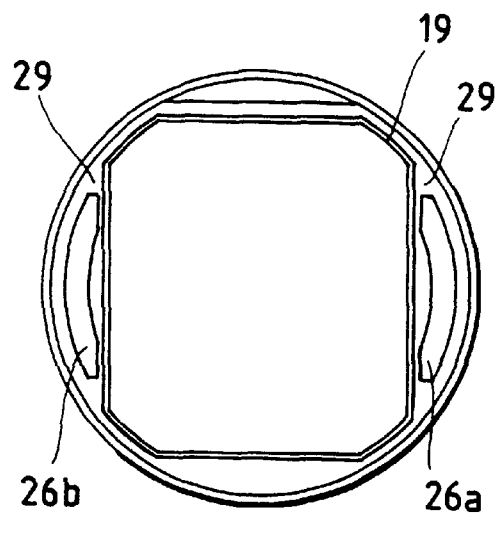
Figure 9A:
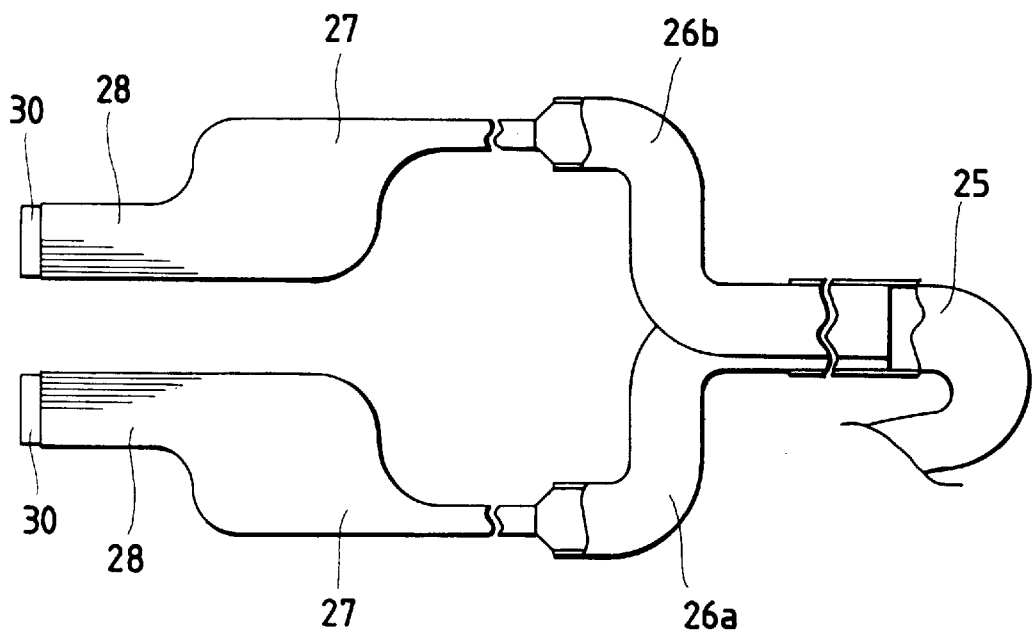
FIGS. 9A and 9B show sectional views illustrating a composition of a light guide to be used in an endoscope which uses the objective optical system according to the present invention.
Figure 9B:
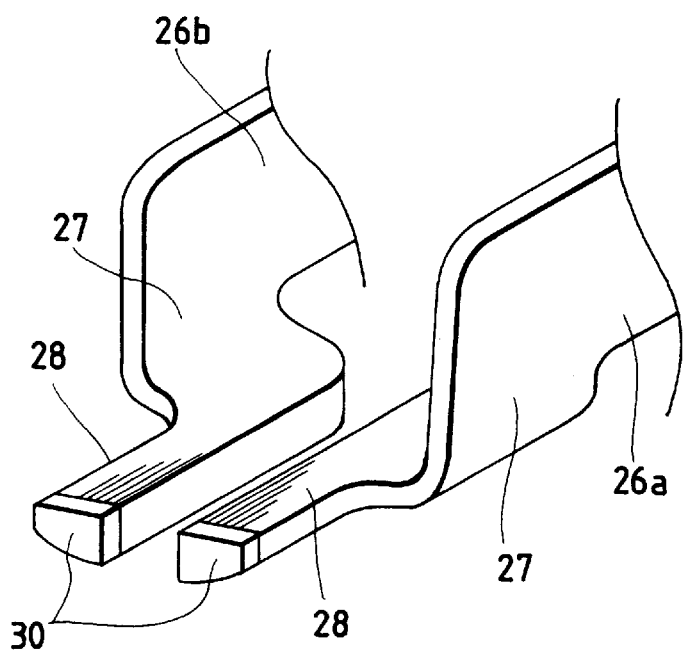

It is desirable that an illumination system for leading illumination light from a light source to the tip adapter type endoscope is configured as shown in FIGS. 8A, 8B, 8C, 9A and 9B. Speaking concretely, the illumination system for the tip of the endoscope according to the present invention is characterized in that a light guide is divided, in a tip frame of an endoscope, into at least two branches each passing in the axial direction of the endoscope and having at least one bending in the tip frame of the endoscope, and that the two branches are formed again into a single light guide. Speaking concretely with reference to FIG. 8A and FIG. 9A, a light guide for leading illumination light from a light source (not shown) is branched into two light guides 26a and 26b in the tip of the endoscope as shown in FIG. 8A and FIG. 9A. As shown in FIG. 8C (sectional view taken along the C—C line in FIG. 8A), the branched light guides 26a and 26b pass through spaces which are not occupied by an image pickup device having a relatively large diameter (spaces between the image pickup device and the outer frame of the endoscope), are bent to have bendings 27 as shown in FIG. 8A and FIG. 9B, and are integrated with each other so as to form a light guide 28 as shown in FIG. 8B (sectional view taken along the B—B line in FIG. 8A).

By configuring a light guide as described above, it is possible to pass a large number of light guides through the tip of the endoscope and use an image pickup device which has a large image size corresponding to the full screen size. Further, by attaching cover glass plates 30 to end surfaces of the branched light guides 26a and 26b as shown in FIG. 9B, it is possible to assure a watertight condition for the lens system, absorb variations of the light guides 16a and 16b in the longitudinal direction and facilitate assembly of the light guides.

Now, the preferred embodiment of the objective optical system for endoscopes according to the present invention will be described below with reference to the accompanying drawings.

The objective optical system for endoscopes according to the present invention uses lens elements having a small diameter as lens elements to be disposed in a tip out of lens elements adopted for composing the optical system, thereby making it possible to pass a large number of optical fibers through light guides composing an illumination optical system, or obtaining a bright illumination optical system. Further, the objective optical system according to the present invention is characterized in that it is configured as the adapter type permitting attaching and detaching adapter units comprising adapter lens system having different field angles, directions toward visual fields, and so on.

Therefore, each of the embodiments described below is an adapter type objective optical system for endoscopes in which an adapter is attached to the optical system according to the present invention (master lens system).

FIGS. 4 through 9 show a first embodiment of the present invention: FIG. 4 showing a composition of a master unit M' (FIG. 6) comprising an objective optical system (master lens system) M, whereas FIG. 5 showing an adapter unit AD' (FIG. 7) comprising an adapter lens system AD, and freely attachable and detachable to and from the master unit M'.

The first embodiment is an example wherein a direct viewing adapter lens system AD having a field angle of 120° is attached to the master lens system M.

In the first embodiment illustrated in FIG. 4, the objective optical system (master lens system) M consists of a lens unit A which is composed of a cover glass plate C2, and a cemented lens component consisting of a negative lens element L4 and a positive lens element L5, and a lens unit B which is composed of a field lens FL. Further, disposed in the objective optical system (master lens system) M are a low pass filter F1, an infrared cut filter F2, a CCD cover glass plate C3 and a CCD image pickup surface 12. The cover glass plate C2 is used for maintaining the objective optical system in a watertight condition, whereas the cover glass plate C3 is adopted for preventing the CCD image pickup surface from being deteriorated. It may be considered, as represented by the reference symbol B in FIGS. 4 and 5, that the lens unit B comprises the field lens FL, the low pass filter F1, the infrared cut filter F2 and the cover glass plate C3. These optical elements have a diameter which is substantially equal to that of the image pickup surface, whereas the lens unit A has a diameter smaller than that of the lens unit B.

The adapter lens system AD which is freely attachable and detachable to and from the objective optical system (master lens system) M in FIG. 5 is composed of a negative lens element L1, a cemented lens component which consists of a positive lens element L2 and a negative lens element L3, and a cover glass plate C1. This adapter lens system AD uses, in addition to the negative lens element L1, the cemented lens component consisting of the lens elements L2 and L3 for correcting chromatic aberration, curvature of field and astigmatism to levels at which these aberrations pose no problem in practical use of the objective optical system. Further, the cover glass plate C1 is disposed for maintaining the adapter lens system in a watertight condition, thereby preventing a visual field from being dimmed by water vapor, etc. The adapter lens system has a small diameter like the lens unit A.

In the first embodiment, the adapter lens system AD is attached to the objective optical system (master lens system) M for obtaining a wide field angle of 120° so that the objective optical system is efficiently usable for a far visual field or an object located at a relatively long distance. For this embodiment, an illumination system is to be composed as already described above with reference to FIGS. 8A, 8B, 8C, 9A and 9B.

The first embodiment has numerical data listed below:

first embodiment
f = 0.582, image height = 0.5055,
object distance = −8.0860

| | | | |
|---|---|---|---|
| $r_1 = \infty$ | | | |
| | $d_1 = 0.0886$ | $n_1 = 1.88300$ | $v_1 = 40.78$ |
| $r_2 = 0.3372$ | | | |
| | $d_2 = 0.1440$ | | |
| $r_3 = 0.7794$ | | | |
| | $d_3 = 0.3988$ | $n_2 = 1.76182$ | $v_2 = 26.55$ |
| $r_4 = -0.3285$ | | | |
| | $d_4 = 0.1130$ | $n_3 = 1.60342$ | $v_3 = 38.01$ |
| $r_5 = -1.9389$ | | | |
| | $d_5 = 0.0066$ | | |
| $r_6 = \infty$ (stop) | | | |
| | $d_6 = 0.0886$ | $n_4 = 1.88300$ | $v_4 = 40.78$ |
| $r_7 = \infty$ | | | |
| | $d_7 = 0.0576$ | | |
| $r_8 = \infty$ | | | |
| | $d_8 = 0.0886$ | $n_5 = 1.51633$ | $v_5 = 64.15$ |
| $r_9 = \infty$ | | | |
| | $d_9 = 0.0443$ | | |
| $r_{10} = -2.1850$ | | | |
| | $d_{10} = 0.0665$ | $n_6 = 1.78472$ | $v_6 = 25.71$ |
| $r_{11} = 0.5047$ | | | |
| | $d_{11} = 0.3434$ | $n_7 = 1.69680$ | $v_7 = 55.53$ |
| $r_{12} = -0.8824$ | | | |
| | $d_{12} = 0.2437$ | | |
| $r_{13} = 1.1630$ | | | |
| | $d_{13} = 0.9260$ | $n_8 = 1.72916$ | $v_8 = 54.68$ |

-continued first embodiment
f = 0.582, image height = 0.5055,
object distance = −8.0860

| | | | |
|---|---|---|---|
| $r_{14} = \infty$ | | | |
| | $d_{14} = 0.1772$ | $n_9 = 1.54814$ | $v_9 = 45.78$ |
| $r_{15} = \infty$ | | | |
| | $d_{15} = 0.3545$ | $n_{10} = 1.51400$ | $v_{10} = 75.00$ |
| $r_{16} = \infty$ | | | |
| | $d_{16} = 0.1661$ | $n_{11} = 1.49700$ | $v_{11} = 81.61$ |
| $r_{17} = \infty$ | | | |
| | $d_{17} = 0.0410$ | | |
| $r_{18} = \infty$ (image) | | | |

$f_M=1$, $f_A=2.856$, $f_B=1.594$, $f_A/f_B=1.792$ $f_A/f_M=2.856$

Figure 10:
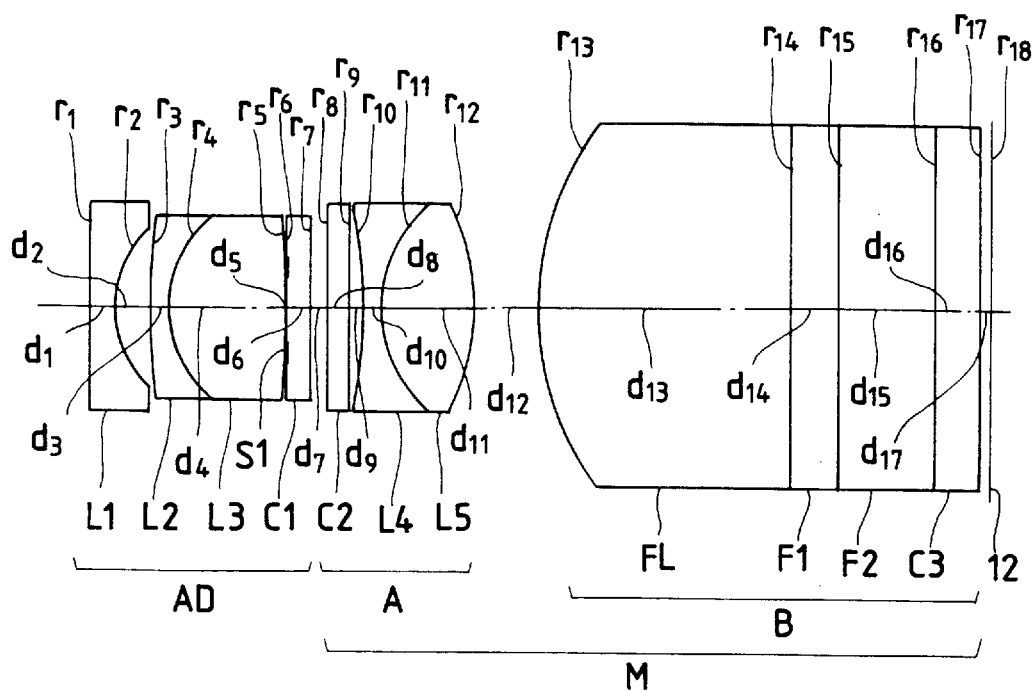
FIGS. 10 through 12 show sectional views illustrating compositions of second through fourth embodiments of the objective optical system for endoscopes according to the present invention.

A second embodiment of the objective optical system according to the present invention has a composition illustrated in FIG. 10, wherein an adapter lens system is attached to a master lens system as in FIG. 5. An objective optical system (master lens system) M used in the second embodiment is the same as that adopted in the first embodiment. The second embodiment adopts an adapter lens system AD which is composed of a negative lens element L1, a cemented lens component which consists of lens elements L2 and L3, and an aperture stop. The adapter lens system used in the second embodiment is different from that adopted for the first embodiment in that the former is composed of a negative lens element L2 and a positive lens element L3 which are disposed in order from the object side. The reference symbol C1 used in FIG. 10 represents a cover glass plate. The adapter lens system has a field angle of 80° and is configured for direct viewing.

The second embodiment has the following numerical data;

second embodiment
f = 0.794, image height = 0.5055,
object distance = −21.0456

| | | | |
|---|---|---|---|
| $r_1 = \infty$ | | | |
| | $d_1 = 0.0886$ | $n_1 = 1.51633$ | $v_1 = 64.15$ |
| $r_2 = 0.3932$ | | | |
| | $d_2 = 0.1329$ | | |
| $r_3 = 3.4298$ | | | |
| | $d_3 = 0.0665$ | $n_2 = 1.51633$ | $v_2 = 64.15$ |
| $r_4 = 0.4338$ | | | |
| | $d_4 = 0.4209$ | $n_3 = 1.88300$ | $v_3 = 40.78$ |
| $r_5 = -7.9322$ | | | |
| | $d_5 = 0.0066$ | | |
| $r_6 = \infty$ (stop) | | | |
| | $d_6 = 0.0886$ | $n_4 = 1.88300$ | $v_4 = 40.78$ |
| $r_7 = \infty$ | | | |
| | $d_7 = 0.0576$ | | |
| $r_8 = \infty$ | | | |
| | $d_8 = 0.0886$ | $n_5 = 1.51633$ | $v_5 = 64.15$ |
| $r_9 = \infty$ | | | |
| | $d_9 = 0.0443$ | | |
| $r_{10} = -2.1850$ | | | |
| | $d_{10} = 0.0665$ | $n_6 = 1.78472$ | $v_6 = 25.71$ |
| $r_{11} = 0.5047$ | | | |
| | $d_{11} = 0.3434$ | $n_7 = 1.69680$ | $v_7 = 55.53$ |
| $r_{12} = -0.8824$ | | | |
| | $d_{12} = 0.2437$ | | |
| $r_{13} = 1.1630$ | | | |
| | $d_{13} = 0.9260$ | $n_8 = 1.72916$ | $v_8 = 54.68$ |
| $r_{14} = \infty$ | | | |
| | $d_{14} = 0.1772$ | $n_9 = 1.54814$ | $v_9 = 45.78$ |
| $r_{15} = \infty$ | | | |
| | $d_{15} = 0.3545$ | $n_{10} = 1.51400$ | $v_{10} = 75.00$ |

-continued second embodiment
f = 0.794, image height = 0.5055,
object distance = −21.0456

| | | | |
|---|---|---|---|
| $r_{16} = \infty$ | | | |
| | $d_{16} = 0.1661$ | $n_{11} = 1.49700$ | $v_{11} = 81.61$ |
| $r_{17} = \infty$ | | | |
| | $d_{17} = 0.0410$ | | |
| $r_{18} = \infty$ (image) | | | |

$f_M=1$, $f_A=2.886$, $f_B=1.594$, $f_A/f_B=1.792$, $f_A/f_M=2.856$

Figure 11:
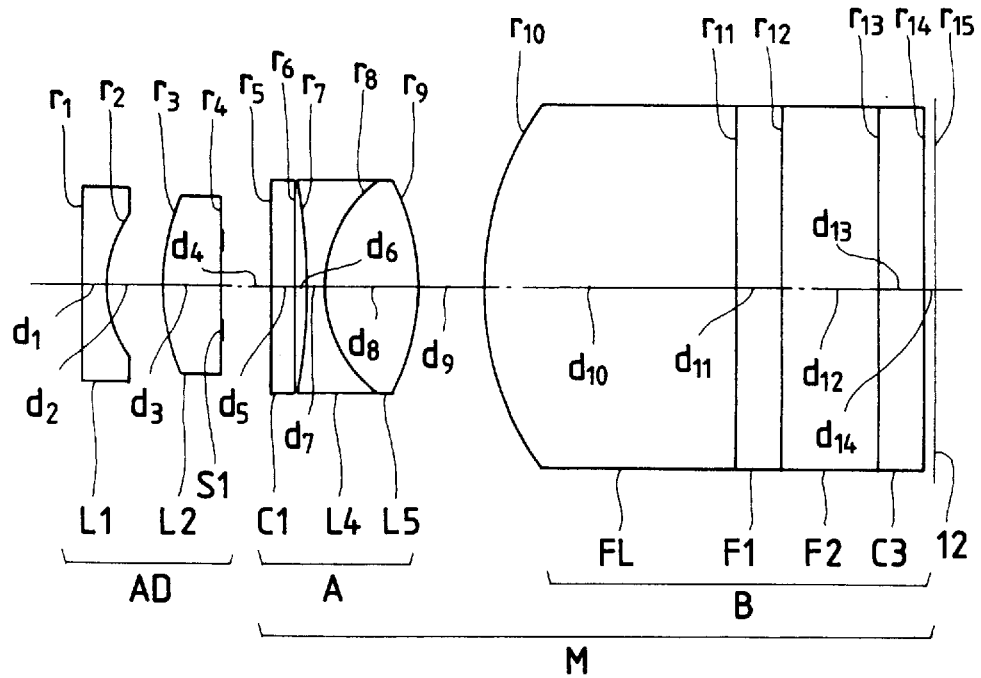

A third embodiment of the objective optical system according to the present invention has a composition shown in FIG. 11, wherein an adapter lens system AD is attached to an objective lens system M. This master lens system selected for the third embodiment is also the same as that used in the first or second embodiment.

Further, the adapter lens system AD is composed, in order from the object side, of a negative lens element L1, a positive lens element L2 and an aperture stop, and is configured as a direct-viewing adapter lens system having a field angle of 80°. This adapter lens system corrects aberrations to practically allowable levels and uses a single lens element in place of the cemented lens component used in the second embodiment. Further, an image side surface of the positive lens element L2 is configured as a planar surface for enhancing adherability to the aperture stop and eliminating the necessity of a cover glass plate which would otherwise be used for maintaining the adapter lens system in a watertight condition. The third embodiment requires a smaller number of parts and uses no cemented lens component, thereby eliminating a cementing step and remarkably lowering a manufacturing cost of the objective optical system.

This adapter lens system may be configured so as to intentionally tilt an image surface on the positive side so that the objective optical system is used exclusively for observing pipes. Further, the adapter lens system may be adjusted so that the third embodiment is to be used exclusively for observing objects located at short distances or long distances as described above. In other words, it is possible to change a location of focus and an observation range by adjusting an airspace reserved in the adapter lens system (airspace $d_2$ between the lens elements L1 and L2) and varying a diameter of the aperture stop at the same time.

Listed below is numerical data of the third embodiment:

third embodiment
f = 0.817, image height = 0.5055,
object distance = −21.045

| | | | |
|---|---|---|---|
| $r_1 = \infty$ | | | |
| | $d1 = 0.0886$ | $n_1 = 1.51633$ | $v_1 = 64.15$ |
| $r_2 = 0.4836$ | | | |
| | $d_2 = 0.2039$ | | |
| $r_3 = 0.8595$ | | | |
| | $d_3 = 0.2127$ | $n_2 = 1.78472$ | $v_2 = 25.71$ |
| $r_4 = \infty$ (stop) | | | |
| | $d_4 = 0.1817$ | | |
| $r_5 = \infty$ | | | |
| | $d_5 = 0.0886$ | $n_3 = 1.51633$ | $v_3 = 64.15$ |
| $r_6 = \infty$ | | | |
| | $d_6 = 0.0443$ | | |
| $r_7 = -2.1850$ | | | |
| | $d_7 = 0.0665$ | $n_4 = 1.78472$ | $v_4 = 25.71$ |
| $r_8 = 0.5047$ | | | |
| | $d_8 = 0.3434$ | $n_5 = 1.69680$ | $v_5 = 55.53$ |

-continued third embodiment
f = 0.817, image height = 0.5055,
object distance = −21.045

| | | | |
|---|---|---|---|
| $r_9 = -0.8824$ | | | |
| | $d_9 = 0.2437$ | | |
| $r_{10} = 1.1630$ | | | |
| | $d_{10} = 0.9260$ | $n_6 = 1.72916$ | $v_6 = 54.68$ |
| $r_{11} = \infty$ | | | |
| | $d_{11} = 0.1772$ | $n_7 = 1.54814$ | $v_7 = 45.78$ |
| $r_{12} = \infty$ | | | |
| | $d_{12} = 0.3545$ | $n_8 = 1.51400$ | $v_8 = 75.00$ |
| $r_{13} = \infty$ | | | |
| | $d_{13} = 0.1661$ | $n_9 = 1.49700$ | $v_9 = 81.61$ |
| $r_{14} = \infty$ | | | |
| | $d_{14} = 0.0410$ | | |
| $r_{15} = \infty$ (image) | | | |

$f_M=1$, $f_A=2.856$, $f_B=1.594$, $f_A/f_B=1.792$, $f_A/f_M=2.856$

Figure 12:
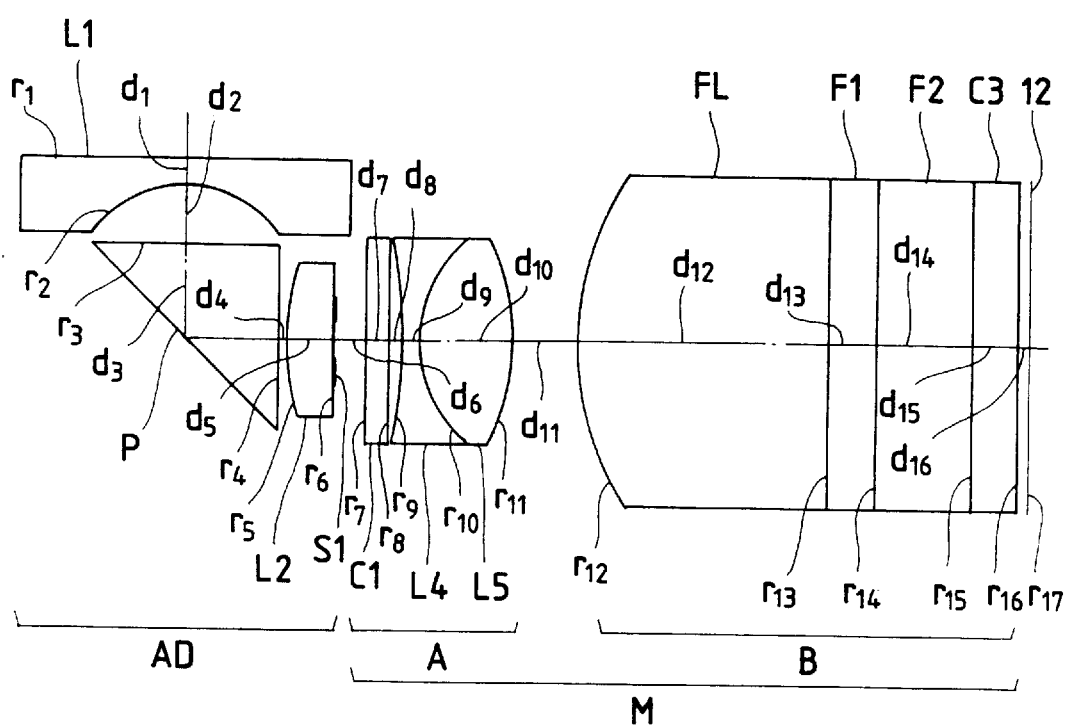

An objective optical system preferred as a fourth embodiment of the present invention has a composition shown in FIG. 12, wherein an adapter lens system configured for side-viewing is attached to an objective optical system (master lens system) M. The adapter lens system is composed, in order from the object side, of a negative lens element L1, a visual field changing prism P, a positive lens element L2 and an aperture stop S1. The objective optical system (master lens system) M is the same as that used in the first, second or third embodiment.

The fourth embodiment is an optical system in which a side-viewing adapter lens system having a field angle of 120° is attached to the objective optical system (master lens system) M. The fourth embodiment which comprises the visual field changing prism P and permits side viewing is suited in particular for observing inside surfaces of pipes, outside surfaces of heat exchange pipes of nuclear reactors and so on.

Figure 13A:
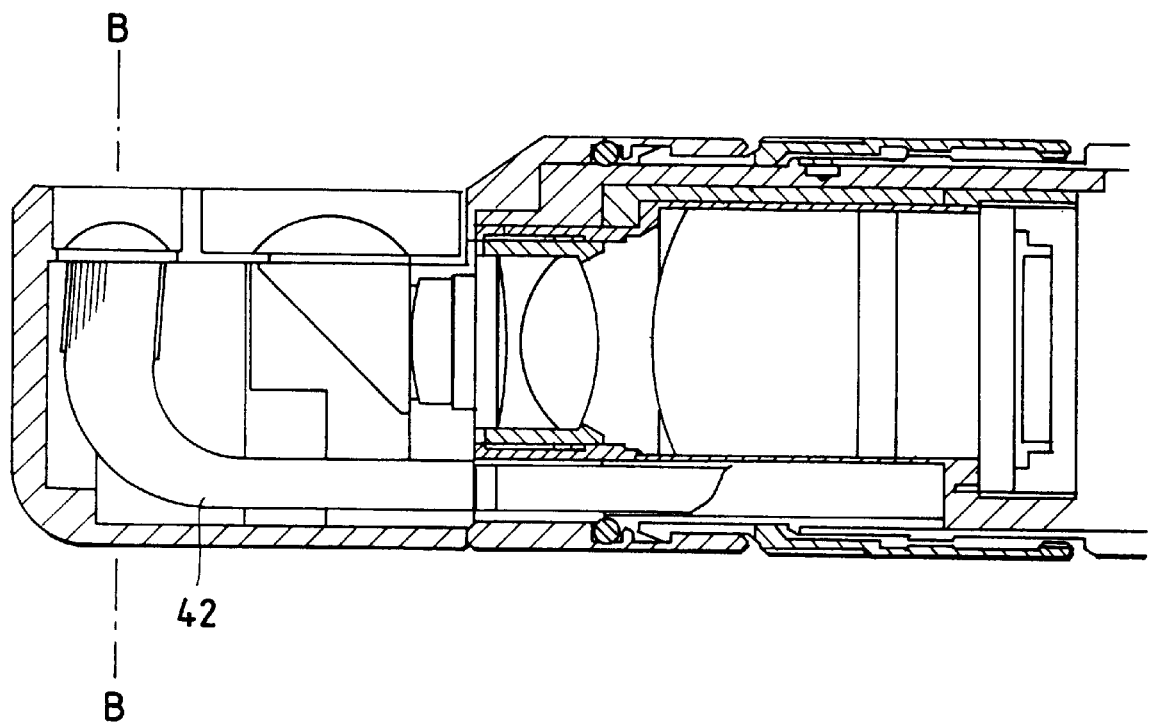
FIGS. 13A and 13B show sectional views illustrating a composition of a tip of an endoscope which comprises the fourth embodiment of the present invention and a light guide.
Figure 13B:
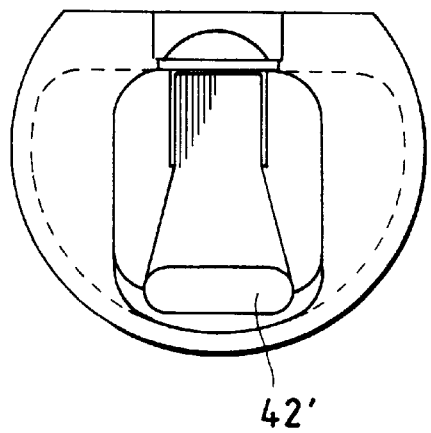

FIGS. 13A and 13B show an example wherein the tip illumination system described above is applied to the optical system preferred as the fourth embodiment. A light guide 42 used in an adapter lens system shown in FIG. 13A may be formed by molding. Further, it is desirable that the light guide 42 has an end surface 42', on a side of a light source, which has a shape substantially matched with that of a light guide disposed in a master lens system M as shown in FIG. 13B (sectional view taken along the B—B line in FIG. 13A) for minimizing loss of illumination light coming from a master unit when the adapter lens unit is attached. This shape of the light guide is applicable also to an optical system to which a direct-viewing adapter lens system is attached. Further, it is desirable that the light guide has a nearly circular end surface on the object side. Since a circular end surface is capable of minimizing loss of the illumination light and ununiformity of illumination, the end surface should desirably have a nearly circular shape.

Selected for the fourth embodiment is the following numerical data:

fourth embodiment
f = 0.563, image height = 0.5055,
object distance = −5.0953

| | | | |
|---|---|---|---|
| $r_1 = \infty$ | | | |
| | $d_1 = 0.0997$ | $n_1 = 1.51633$ | $v_1 = 64.15$ |
| $r_2 = 0.4218$ | | | |
| | $d_2 = 0.2193$ | | |

-continued fourth embodiment
f = 0.563, image height = 0.5055,
object distance = −5.0953

| | | | |
|---|---|---|---|
| $r_3 = \infty$ | | | |
| | $d_3 = 0.6868$ | $n_2 = 1.84666$ | $v_2 = 23.78$ |
| $r_4 = \infty$ | | | |
| | $d_4 = 0.0222$ | | |
| $r_5 = 1.0326$ | | | |
| | $d_5 = 0.1772$ | $n_3 = 1.78472$ | $v_3 = 25.71$ |
| $r_6 = \infty$ (stop) | | | |
| | $d_6 = 0.1108$ | | |
| $r_7 = \infty$ | | | |
| | $d_7 = 0.0886$ | $n_4 = 1.51633$ | $v_4 = 64.15$ |
| $r_8 = \infty$ | | | |
| | $d_8 = 0.0443$ | | |
| $r_9 = -2.1850$ | | | |
| | $d_9 = 0.0665$ | $n_5 = 1.78472$ | $v_5 = 25.71$ |
| $r_{10} = 0.5047$ | | | |
| | $d_{10} = 0.3434$ | $n_6 = 1.69680$ | $v_6 = 55.53$ |
| $r_{11} = -0.8824$ | | | |
| | $d_{11} = 0.2437$ | | |
| $r_{12} = 1.1630$ | | | |
| | $d_{12} = 0.9260$ | $n_7 = 1.72916$ | $v_7 = 54.68$ |
| $r_{13} = \infty$ | | | |
| | $d_{13} = 0.1772$ | $n_8 = 1.54814$ | $v_8 = 45.78$ |
| $r_{14} = \infty$ | | | |
| | $d_{14} = 0.3545$ | $n_9 = 1.51400$ | $v_9 = 75.00$ |
| $r_{15} = \infty$ | | | |
| | $d_{15} = 0.1661$ | $n_{10} = 1.49700$ | $v_{10} = 81.61$ |
| $r_{16} = \infty$ | | | |
| | $d_{16} = 0.0410$ | | |
| $r_{17} = \infty$ (image) | | | |

$f_M=1$, $f_A=2.856$, $f_B=1.594$, $f_A/f_B=1.792$, $f_A/f_M=2.856$

Figure 14:
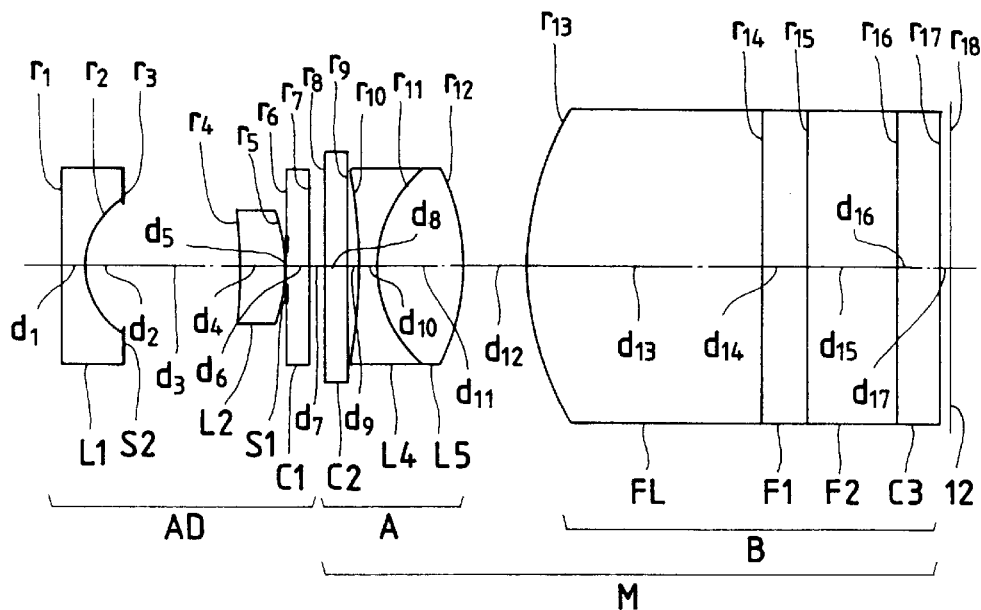
FIGS. 14 through 19 show sectional views illustrating compositions of fifth through tenth embodiments respectively of the objective optical system for endoscopes according to the present invention.

A fifth embodiment of the present invention has a composition illustrated in FIG. 14 wherein an adapter lens system is composed of a negative lens element L1, a field stop S2, a positive lens element L2, an aperture stop S1 and a cover glass plate C1. The fifth embodiment is an example wherein a direct-viewing adapter lens system having a field angle of 120° is attached to a master lens system M. In this embodiment, a focal length of an objective optical system is shortened by restricting only a portion of an entire image area. The fifth embodiment therefore makes it possible to obtain a range of observation depth which is broader than that obtainable with any one of the first through fourth embodiments. The first or fourth embodiment provides a field angle of 120° in a diagonal direction of an image area but has a field angle as narrow as approximately 70° in a direction along a shorter side.

The fifth embodiment which restricts the image area in a direction nearly matched with the shorter side of a monitor screen provides a merit that it permits observing a tubular object such as a pipe in all directions nearly at the same time within a circular visual field having a field angle of 120°.

Listed below is numerical data selected for configuring the fifth embodiment:

fifth embodiment
f = 0.323, image height = 0.2880,
object distance = −1.7058

| | | | |
|---|---|---|---|
| $r_1 = \infty$ | | | |
| | $d_1 = 0.0886$ | $n_1 = 1.88300$ | $v_1 = 40.78$ |
| $r_2 = 0.3152$ | | | |
| | $d_2 = 0.1196$ | | |
| $r_3 = \infty$ (field stop) | | | |
| | $d_3 = 0.4896$ | | |

-continued fifth embodiment
f = 0.323, image height = 0.2880,
object distance = −1.7058

| | | | |
|---|---|---|---|
| $r_4 = -2.9903$ | | | |
| | $d_4 = 0.1772$ | $n_1 = 1.84666$ | $v_2 = 23.78$ |
| $r_5 = -0.6927$ | | | |
| | $d_5 = 0.0066$ | | |
| $r_6 = \infty$ (stop) | | | |
| | $d_6 = 0.0886$ | $n_3 = 1.88300$ | $v_3 = 40.78$ |
| $r_7 = \infty$ | | | |
| | $d_7 = 0.0576$ | | |
| $r_8 = \infty$ | | | |
| | $d_8 = 0.0886$ | $n_4 = 1.51633$ | $v_4 = 64.15$ |
| $r_9 = \infty$ | | | |
| | $d_9 = 0.0443$ | | |
| $r_{10} = -2.1850$ | | | |
| | $d_{10} = 0.0665$ | $n_5 = 1.78472$ | $v_5 = 25.71$ |
| $r_{11} = 0.5047$ | | | |
| | $d_{11} = 0.3434$ | $n_6 = 1.69680$ | $v_6 = 55.53$ |
| $r_{12} = -0.8824$ | | | |
| | $d_{12} = 0.2437$ | | |
| $r_{13} = 1.1630$ | | | |
| | $d_{13} = 0.9260$ | $n_7 = 1.72916$ | $v_7 = 54.68$ |
| $r_{14} = \infty$ | | | |
| | $d_{14} = 0.1772$ | $n_8 = 1.54814$ | $v_8 = 45.78$ |
| $r_{15} = \infty$ | | | |
| | $d_{15} = 0.3545$ | $n_9 = 1.51400$ | $v_9 = 75.00$ |
| $r_{16} = \infty$ | | | |
| | $d_{16} = 0.1661$ | $n_{10} = 1.49700$ | $v_{10} = 81.61$ |
| $r_{17} = \infty$ | | | |
| | $d_{17} = 0.0410$ | | |
| $r_{18} = \infty$ (image) | | | |

$f_M=1$, $f_A=2.856$, $f_B=1.594$, $f_A/f_B=1.792$, $f_A/f_M=2.856$

Figure 15:
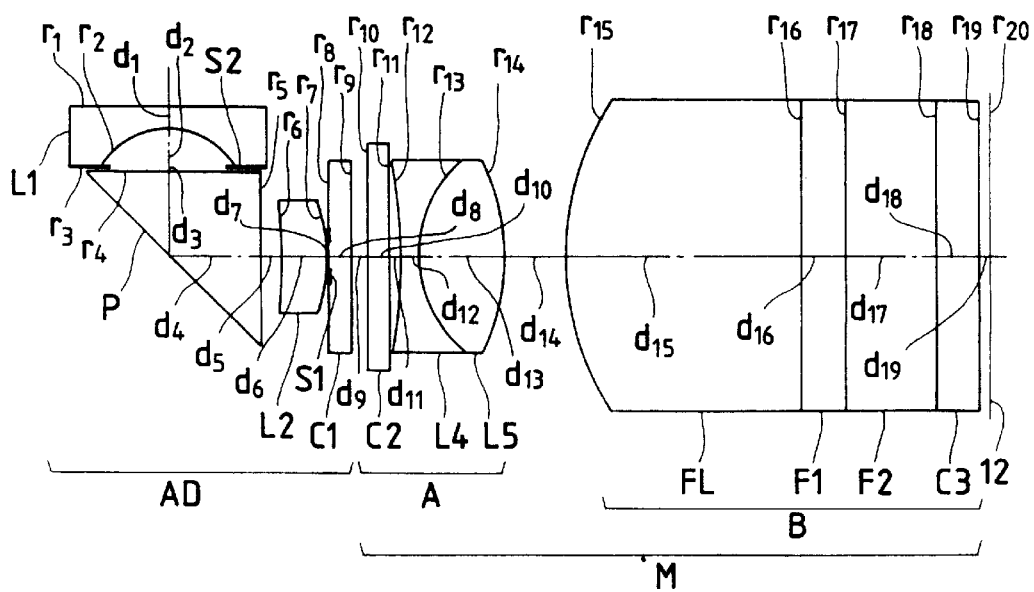

A sixth embodiment of the present invention has a composition illustrated in FIG. 15. In this embodiment, an adapter lens system is composed, in order from the object side, of a negative lens element L1, a field stop S2, a visual field changing prism P, a positive lens element L2, an aperture stop S1 and a cover glass plate C1.

The sixth embodiment is configured as a side-viewing objective optical system by adding the visual field changing prism P to the adapter lens system which is used in the fifth embodiment. Since the adapter lens system selected for the sixth embodiment has an observation range broader than that of the side-viewing adapter lens system used in the fourth embodiment, it provides a merit that the sixth embodiment can be placed closer to an object for observation.

The sixth embodiment has numerical data listed below:

sixth embodiment
f = 0.321, image = 0.2880,
object distance = −1.7058

| | | | |
|---|---|---|---|
| $r_1 = \infty$ | | | |
| | $d_1 = 0.0886$ | $n_1 = 1.88300$ | $v_1 = 40.78$ |
| $r_2 = 0.3152$ | | | |
| | $d_2 = 0.1196$ | | |
| $r_3 = \infty$ (field stop) | | | |
| | $d_3 = 0.0443$ | | |
| $r_4 = \infty$ | | | |
| | $d_4 = 0.6868$ | $n_2 = 1.84666$ | $v_2 = 23.78$ |
| $r_5 = \infty$ | | | |
| | $d_5 = 0.0775$ | | |
| $r_6 = -2.9903$ | | | |
| | $d_6 = 0.1772$ | $n_3 = 1.84666$ | $v_3 = 23.78$ |
| $r_7 = -0.6927$ | | | |
| | $d_7 = 0.0066$ | | |
| $r_8 = \infty$ (stop) | | | |
| | $d_8 = 0.0886$ | $n_4 = 1.88300$ | $v_4 = 40.78$ |

-continued sixth embodiment
f = 0.321, image = 0.2880,
object distance = −1.7058

| | | | |
|---|---|---|---|
| $r_9 = \infty$ | | | |
| | $d_9 = 0.0576$ | | |
| $r_{10} = \infty$ | | | |
| | $d_{10} = 0.0886$ | $n_5 = 1.51633$ | $v_5 = 64.15$ |
| $r_{11} = \infty$ | | | |
| | $d_{11} = 0.0443$ | | |
| $r_{12} = -2.1850$ | | | |
| | $d_{12} = 0.0665$ | $n_6 = 1.78472$ | $v_6 = 25.71$ |
| $r_{13} = 0.5047$ | | | |
| | $d_{13} = 0.3434$ | $n_7 = 1.69680$ | $v_7 = 55.53$ |
| $r_{14} = -0.8824$ | | | |
| | $d_{14} = 0.2437$ | | |
| $r_{15} = 1.1630$ | | | |
| | $d_{15} = 0.9260$ | $n_8 = 1.72916$ | $v_8 = 54.68$ |
| $r_{16} = \infty$ | | | |
| | $d_{16} = 0.1772$ | $n_9 = 1.54814$ | $v_9 = 45.78$ |
| $r_{17} = \infty$ | | | |
| | $d_{17} = 0.3545$ | $n_{10} = 1.51400$ | $v_{10} = 75.00$ |
| $r_{18} = \infty$ | | | |
| | $d_{18} = 0.1661$ | $n_{11} = 1.49700$ | $v_{11} = 81.61$ |
| $r_{19} = \infty$ | | | |
| | $d_{19} = 0.0410$ | | |
| $r_{20} = \infty$ (image) | | | |

$f_M=1$, $f_A=2.856$, $f_B=1.594$, $f_A/f_B=1.792$, $f_A/f_M=2.856$

The objective optical system (master lens system) M is common to all the first through sixth embodiments described above.

Figure 16:
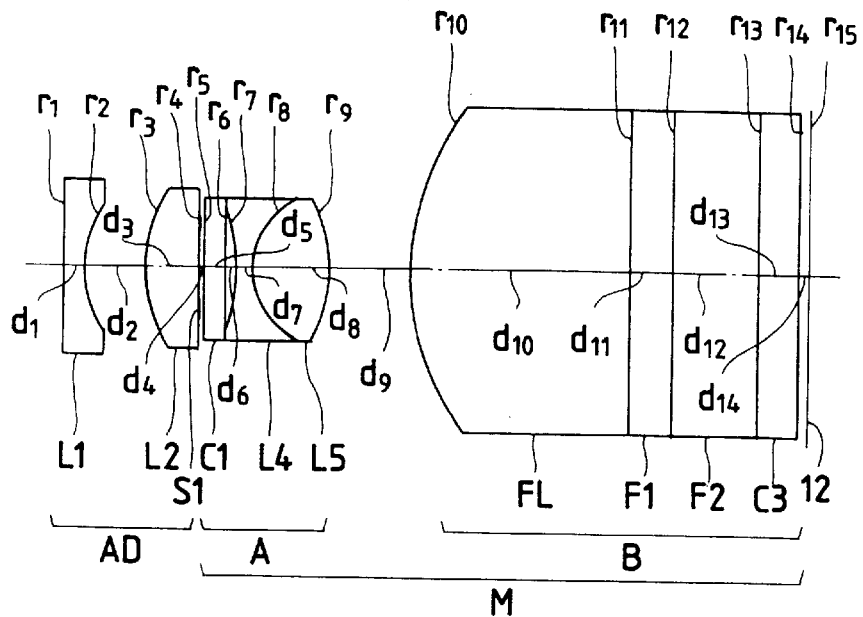

A seventh embodiment of the present invention has a composition illustrated in FIG. 16, wherein an objective optical system (master lens system) M is composed, in order from the object side, of a lens unit A which is composed of a cemented lens component consisting of a negative lens element L4 and a positive lens element L5 and a lens unit B which is composed of a field lens FL. Further, the seventh embodiment additionally comprises a cover glass plate C1, a low pass filter F1, an infrared cut filter F2, a CCD cover glass plate C3 and a CCD image pickup surface.

An adapter lens system adopted for the seventh embodiment is composed, in order from the object side, of a negative lens element L1, a positive lens element L2 and an aperture stop S1.

In the seventh embodiment, the objective optical system (master lens system) M is configured so as to have an outside diameter as small as possible while satisfying the conditions (1) and (2) so that an increased number of light guides can pass therethrough. It is undesirable to configure the lens unit A so as to have a smaller outside diameter since such an outside diameter will allow eclipse of a visual field, production of flare, etc. and aggravation of aberrations to unallowable levels. Attached to the objective optical system (master lens system) M is an adapter lens system having a field angle of 80°.

The seventh embodiment has the following numerical data:

seventh embodiment
f = 0.727, image height = 0.4567,
object distance = −19.0114

| | | | |
|---|---|---|---|
| $r_1 = \infty$ | | | |
| | $d_1 = 0.0800$ | $n_1 = 1.51633$ | $v_1 = 64.15$ |
| $r_2 = 0.4400$ | | | |
| | $d_2 = 0.2239$ | | |

-continued seventh embodiment
f = 0.727, image height = 0.4567,
object distance = −19.0114

| | | | |
|---|---|---|---|
| $r_3 = 0.5969$ | | | |
| | $d_3 = 0.1990$ | $n_2 = 1.78472$ | $v_2 = 25.71$ |
| $r_4 = \infty$ (stop) | | | |
| | $d_4 = 0.0155$ | | |
| $r_5 = \infty$ | | | |
| | $d_5 = 0.0800$ | $n_3 = 1.51633$ | $v_3 = 64.15$ |
| $r_6 = \infty$ | | | |
| | $d_6 = 0.0400$ | | |
| $r_7 = -0.7168$ | | | |
| | $d_7 = 0.0600$ | $n_4 = 1.78472$ | $v_4 = 25.71$ |
| $r_8 = 0.2927$ | | | |
| | $d_8 = 0.2882$ | $n_5 = 1.69680$ | $v_5 = 55.53$ |
| $r_9 = -0.5898$ | | | |
| | $d_9 = 0.3002$ | | |
| $r_{10} = 1.0095$ | | | |
| | $d_{10} = 0.8185$ | $n_6 = 1.72916$ | $v_6 = 54.68$ |
| $r_{11} = \infty$ | | | |
| | $d_{11} = 0.1601$ | $n_7 = 1.54814$ | $v_7 = 45.78$ |
| $r_{12} = \infty$ | | | |
| | $d_{12} = 0.3202$ | $n_8 = 1.51400$ | $v_8 = 75.00$ |
| $r_{13} = \infty$ | | | |
| | $d_{13} = 0.1501$ | $n_9 = 1.49700$ | $v_9 = 81.61$ |
| $r_{14} = \infty$ | | | |
| | $d_{14} = 0.0370$ | | |
| $r_{15} = \infty$ (image) | | | |

$f_M=1$, $f_A=9.484$, $f_B=1.010$, $f_A/f_B=9.885$ $f_A/f_M=9.984$, outside diameter of lens unit A=2.4 mm, outside diameter of lens unit B=5.4 mm, (outside diameter of lens unit A)/(outside diameter of lens unit B)=0.44

Figure 17:
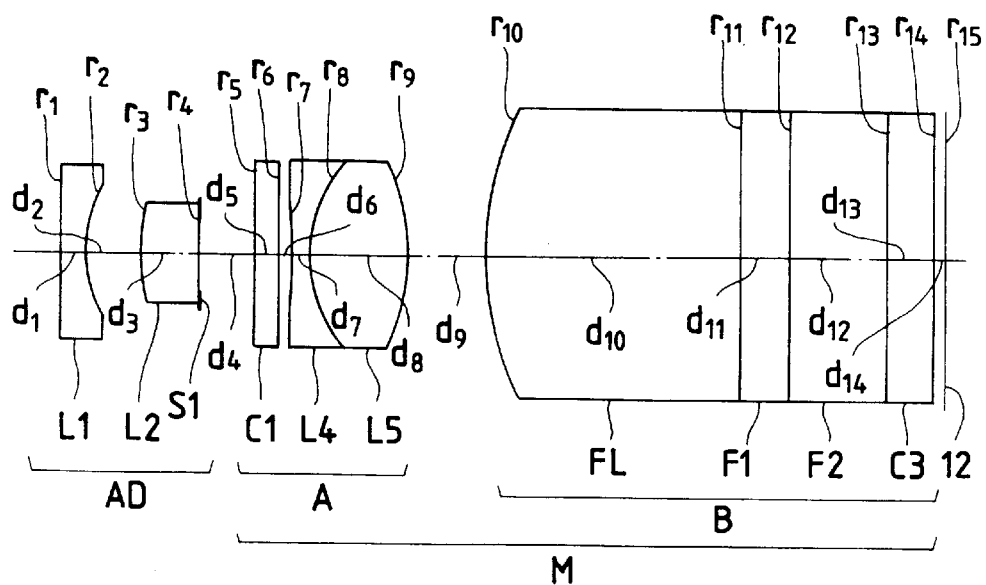

An eighth embodiment of the present invention has a composition illustrated in FIG. 17. In the eighth embodiment, an adapter lens system AD is composed of a negative lens element L1, a positive lens element L2 and an aperture stop S1, whereas an objective optical system (master lens system) M is composed of a lens unit A which is composed of a cover glass plate C2, a cemented lens component consisting of a negative lens element L4 and a positive lens element L5, and a lens unit B which is composed of a field lens FL, a low pass filter F1, an infrared cut filter F2, a CCD cover glass plate C3 and a CCD image pickup surface.

In the eighth embodiment also, the lens unit A disposed in the master lens system M is configured so as to have an outside diameter as small as possible while satisfying the conditions (1) and (2). In the eighth embodiment, it is undesirable to configure the lens unit A so as to have a smaller outside diameter since such an outside diameter will enhance rays on the lens unit B. As a result, it is necessary to enlarge an outside diameter of the lens unit B, thereby producing inconvenience of a necessity to enlarge an outside diameter of a tip of the endoscope or reduce a number of optical fibers to be disposed in light guides. The eighth embodiment is an example wherein an adapter lens system AD which has a field angle of 80° is attached to the master lens system M.

Selected for the eighth embodiment is numerical data which is listed below:

| eighth embodiment<br>f = 0.825, image height = 0.5228,<br>object distance = −21.7640 | | | |
|---|---|---|---|
| $r_1 = \infty$ | | | |
| | $d_1 = 0.0916$ | $n_1 = 1.51633$ | $\nu_1 = 64.15$ |
| $r_2 = 0.4946$ | | | |
| | $d_2 = 0.2108$ | | |
| $r_3 = 0.9964$ | | | |
| | $d_3 = 0.2199$ | $n_2 = 1.78472$ | $\nu_2 = 25.71$ |
| $r_4 = \infty$ (stop) | | | |
| | $d_4 = 0.1983$ | | |
| $r_5 = \infty$ | | | |
| | $d_5 = 0.0916$ | $n_3 = 1.51633$ | $\nu_3 = 64.15$ |
| $r_6 = \infty$ | | | |
| | $d_6 = 0.0458$ | | |
| $r_7 = -3.2009$ | | | |
| | $d_7 = 0.0687$ | $n_4 = 1.78472$ | $\nu_4 = 25.71$ |
| $r_8 = 0.5537$ | | | |
| | $d_8 = 0.3551$ | $n_5 = 1.69680$ | $\nu_5 = 55.53$ |
| $r_9 = -0.9075$ | | | |
| | $d_9 = 0.2978$ | | |
| $r_{10} = 1.2448$ | | | |
| | $d_{10} = 0.9576$ | $n_6 = 1.72916$ | $\nu_6 = 54.68$ |
| $r_{11} = \infty$ | | | |
| | $d_{11} = 0.1833$ | $n_7 = 1.54814$ | $\nu_7 = 45.78$ |
| $r_{12} = \infty$ | | | |
| | $d_{12} = 0.3666$ | $n_8 = 1.51400$ | $\nu_8 = 75.00$ |
| $r_{13} = \infty$ | | | |
| | $d_{13} = 0.1718$ | $n_9 = 1.49700$ | $\nu_9 = 81.61$ |
| $r_{14} = \infty$ | | | |
| | $d_{14} = 0.0424$ | | |
| $r_{15} = \infty$ (image) | | | |

$f_M=1$, $f_A=2.3$, $f_B=1.707$, $f_A/f_B=1.347$, $f_A/f_M=2.3$, outside diameter of lens unit A=3 mm, outside diameter of lens unit B=4.4 mm, (outside diameter of lens unit A)/(outside diameter of lens unit B)=0.68

In each of the seventh and eighth embodiments, it may be considered that the lens unit B used in the master lens system comprises the field lens FL, the low pass filter F1, the infrared cut filter F2 and the cover glass plate C3.

In the numerical data of the first through eighth embodiments described above, the reference symbols $r_1, r_2, \ldots$ represent radii of curvature on respective lens surfaces, the reference symbols $d_1, d_2, \ldots$ designate thicknesses of respective lens elements and airspaces reserved therebetween, the reference symbols $n_1, n_2, \ldots$ denote refractive indices of the respective lens elements, and the reference symbols $\nu_1, \nu_2, \ldots$ represent Abbe's numbers of the respective lens elements. Further, the reference symbol f designates a focal length of the optical system as a whole comprising the adapter lens system and the reference symbol $f_M$ denotes a focal length of the master lens system only. The numerical data is normalized to $f_M=1$.

Out of the embodiments described above, the seventh embodiemnt is configured to have a ratio (outside diameter of lens unit A)/(outside diameter of lens unit B) of 0.44 which is the smallest of all the ratios or a largest difference between the outside diameters of all the differences selected for the embodiments and the eighth embodiment is configured to have a ratio of 0.68 between the outside diameters which is the largest of all the ratios or a smallest difference between the outside diameters of all the differences selected for the embodiments. Ratios between the outside diameters selected for the other embodiments are between the values adopted for the seventh and eighth embodiments.

Figure 18:
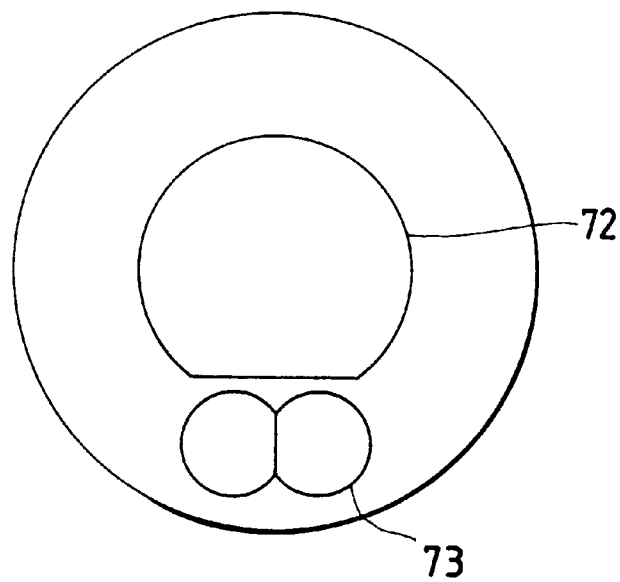

When an adapter lens system type objective optical system such as that according to the present invention uses an adapter lens system having a wider field angle, a lens element which is to be disposed on the object side in the optical system tends to have a large outside diameter. For this reason, it is desirable to select for an endoscope tip such a composition as that adopted for a ninth embodiment of the present invention illustrated in FIG. 18. Schematically shown in this drawing is an adapter lens system which is seen from a side of its tip and has a partially cut objective optical system. Since an image pickup device generally has a rectangular shape, it is unnecessary to shape lens elements circular. Accordingly, a ray which is incident highest on the image pickup device (in a diagonal direction in a visual field) is not eclipsed when an objective optical system 72 is partially cut as shown in FIG. 18. Further the lens element may be rectangular.

When lens elements cannot be laid within a tip frame or when it is desired to configure an endoscope tip thinner, an illumination lens 73 may be composed of parts which are integrated after shaping as shown in FIG. 18. An illumination lens having such a shape may be manufactured by shaping or molding a material such as a resin.

Figure 19:
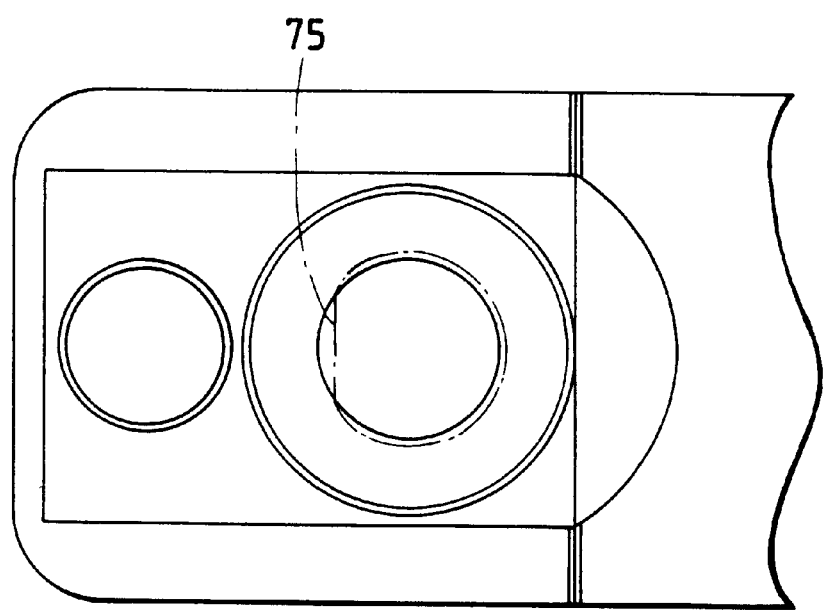

Since the image pickup device is rectangular as described above, circular lens elements are apt to allow flare to be produced by detrimental rays (rays outside a visual field). Accordingly, it is possible to select a composition such as that shown in FIG. 19 illustrating a tenth embodiment of the present invention. Shown in this drawing is a side-viewing adapter lens system as seen from a side of its end surface (from above) which is not circular unlike the ordinary flare stop. Detrimental rays to be incident on an image pickup surface can be eliminated by using a flare stop 75 which has a partially cut circular shape. A plurality of portions of a flare stop may be cut off and a flare stop having such a shape may be used in an objective optical system.

Figure 20:
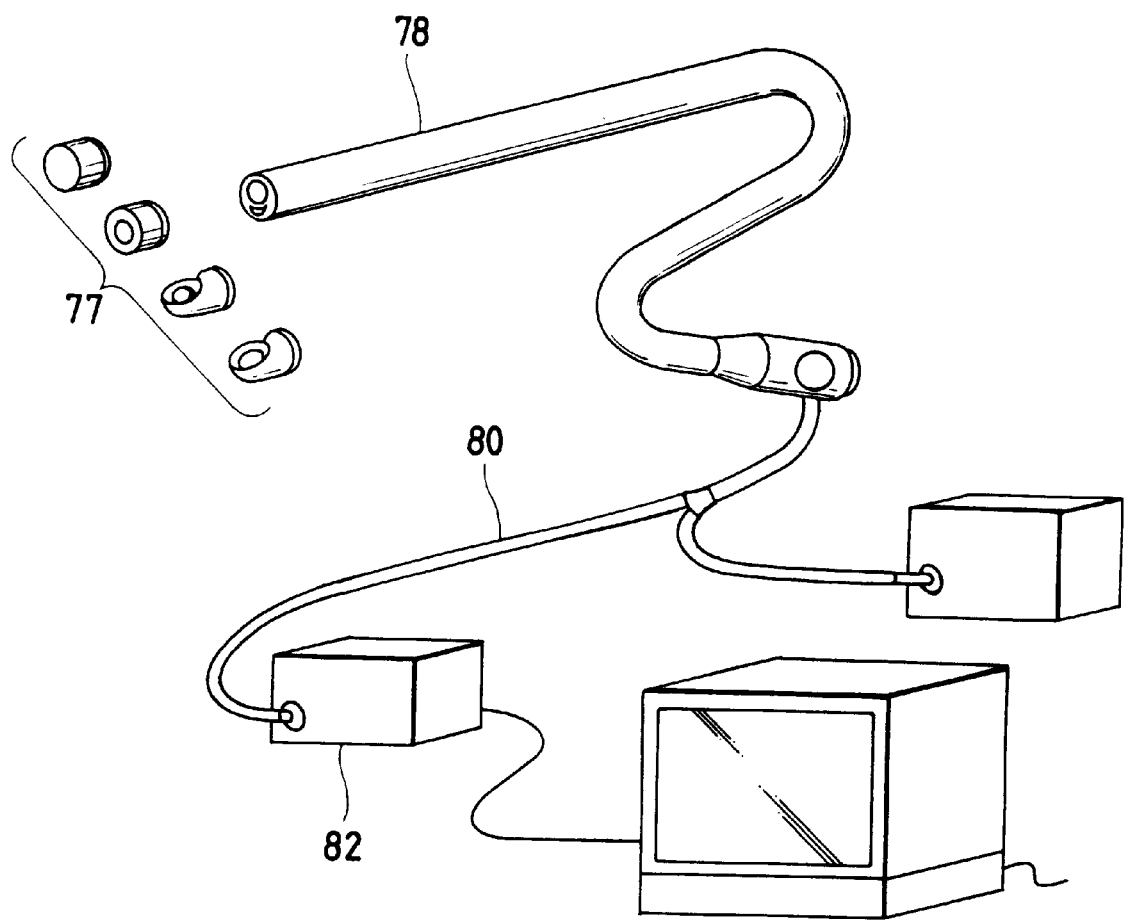
FIG. 20 shows a perspective view descriptive of a tip adapter type endoscope system according to the present invention.

FIG. 20 is a perspective view schematically showing an endoscope system which uses the tip adapter lens system type objective optical system for endoscopes according to the present invention. In this drawing, an adapter that is optimum for an object to be observed is selected from among a group of adapters 77 and attached to an endoscope body 78. In this condition, an image of the object is imaged on a light receiving surface of an image pickup device disposed in the endoscope through the attached adapter lens system and the objective optical system for endoscopes, transferred as image data through a universal cord 80 to a camera control unit 82 for required conversion of the image data, and output to a monitor for display. An illumination light beam emitted from a light source is led through light guides (not shown) so that an illuminator lens disposed in a tip of the endoscope will irradiate the object at proper distribution and intensities.

What is claimed is:

1. An illumination system for an endoscope, comprising:
    a light guide bundle constructed and arranged to illuminate an object to be observed, said light guide bundle being extended in an axial direction of said endoscope and branched into a plurality of branch portions in a frame which is adapted to be disposed inside of said endoscope,
    each of said branch portions having a crescent-shaped cross-section at a mid-portion along said axial direction of said endoscope and each of said branch portions have at least one bent portion.

2. An illumination system for an endoscope, comprising:
    a light guide bundle constructed and arranged to illuminate an object to be observed,
    said light guide bundle being extended in an axial direction of said endoscope and branched into a plurality of branch portions in a frame which is adapted to be disposed inside said endoscope, and wherein each of said plurality of branch portions has a crescent-shaped cross section, said plurality of branch portions being banded together to form an exit surface adapted for said endoscope on a distal end of said endoscope.

3. An illumination system for an endoscope according to claim 2, wherein a protecting glass plate is provided at an end surface of each of said branched light guides.

4. An illumination system for an endoscope according to claim 3, wherein said protecting glass plate has a shape of a portion of a circle.

5. An illumination system for an endoscope according to claim 2, wherein said exit surface comprises a protecting glass plate.

6. An endoscope system, comprising:

an endoscope body;

a universal cord attached to said endoscope body, said universal cord transferring image data from said endoscope body; and a camera control unit in communication with said universal cord, wherein said endoscope body comprises an illumination system, said illumination system comprising:
 a light guide bundle constructed and arranged to illuminate an object to be observed, said light guide bundle being extended in an axial direction of said endoscope and branched into a plurality of branch portions in a frame which is adapted to be disposed inside of said endoscope,
 each of said branch portions having a crescent-shaped cross-section at a mid-portion along said axial direction of said endoscope and each of said branch portions have at least one bent portion.

7. An endoscope system, comprising:

an endoscope body;

a universal cord attached to said endoscope body, said universal cord transferring image data from said endoscope body; and a camera control unit in communication with said universal cord, wherein said endoscope body comprises:
 a light guide bundle constructed and arranged to illuminate an object to be observed,
 said light guide bundle being extended in an axial direction of said endoscope and branched into a plurality of branch portions in a frame which is adapted to be disposed inside said endoscope, and
 wherein each of said plurality of branch portions has a crescent-shaped cross section, said plurality of branch portions being banded together to form an exit surface adapted for said endoscope on a distal end of said endoscope.

8. An endoscope system according to claim 7, wherein a protecting glass plate is provided at an end surface of each of said branched light guides.

9. An endoscope system according to claim 8, wherein said protecting glass plate has a shape of a portion of a circle.

10. An endoscope system according to claim 7, wherein said exit surface comprises a protecting glass plate.

* * * * *